United States Patent
Maierhofer

(10) Patent No.: US 10,639,411 B2
(45) Date of Patent: May 5, 2020

(54) DEVICE FOR IDENTIFYING THE DIRECTION OF LIQUID FLOW THROUGH A DIALYSER

(71) Applicant: FRESENIUS MEDICAL CARE DEUTSCHLAND GMBH, Bad Homburg (DE)

(72) Inventor: Andreas Maierhofer, Schweinfurt (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 37 days.

(21) Appl. No.: 15/328,691

(22) PCT Filed: Jul. 20, 2015

(86) PCT No.: PCT/EP2015/066577
§ 371 (c)(1),
(2) Date: Jan. 24, 2017

(87) PCT Pub. No.: WO2016/016039
PCT Pub. Date: Feb. 4, 2016

(65) Prior Publication Data
US 2017/0209634 A1    Jul. 27, 2017

(30) Foreign Application Priority Data
Aug. 1, 2014 (DE) .................. 10 2014 011 250

(51) Int. Cl.
*A61M 1/16* (2006.01)
(52) U.S. Cl.
CPC ........ *A61M 1/1615* (2014.02); *A61M 1/1609* (2014.02); *A61M 1/1617* (2014.02)
(58) Field of Classification Search
None
See application file for complete search history.

(56) References Cited

U.S. PATENT DOCUMENTS

| | | |
|---|---|---|
| 2012/0298581 A1 | 11/2012 | Wehmeyer et al. |
| 2013/0193039 A1 | 8/2013 | Kopperschmidt |
| 2013/0338560 A1 | 12/2013 | Bene et al. |

FOREIGN PATENT DOCUMENTS

| | | |
|---|---|---|
| DE | 102010032980 A1 | 2/2012 |
| WO | 2012159734 A1 | 11/2012 |

OTHER PUBLICATIONS

Wolf et al, "Artificial kidney function: kinetics of kidney dialysis", Albany Medical College, Jul. 30, 1951.*

(Continued)

*Primary Examiner* — Krishnan S Menon
(74) *Attorney, Agent, or Firm* — Kilyk & Bowersox, P.L.L.C.

(57) ABSTRACT

The invention relates to a device and a method for detecting the direction of fluid flow through a dialyser 1 which comprises a blood chamber 4, through which blood flows, and a dialysate chamber 3, through which dialysate flows, which are separated from one another by a semi-permeable membrane 2. In addition, the invention relates to an extracorporeal blood treatment device comprising a device for detecting the flow direction. A first aspect of the invention is to measure the clearance in order to detect the flow direction and to compare the measured clearance with a specified limit value, a flow direction in countercurrent flow being concluded if the clearance is greater than the specified limit value. This aspect is based on the finding that in the case of blood treatment in practice with operation of the dialyser in co-current flow, clearance values above a certain limit value can no longer be achieved. A second aspect of the invention is to measure the clearance to detect the flow direction and to change the flow rate of the dialysate. Checking the flow direction according to the second aspect is based on the comparison of the measured change in clearance with a calculated expected value of the change in clearance for (Continued)

Figure 1:
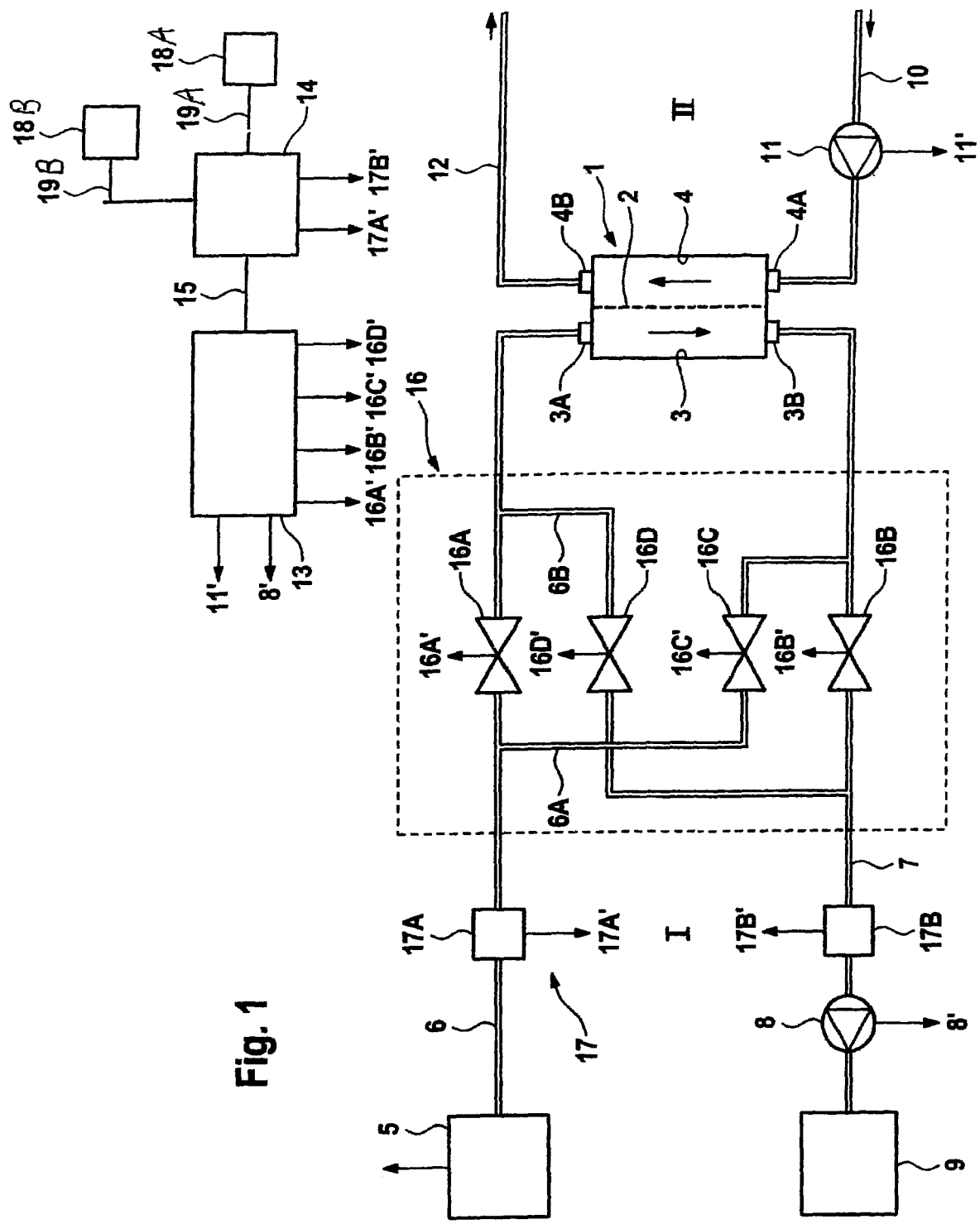

operation of the dialyser in both countercurrent flow and co-current flow. The invention according to the second aspect is based on the finding that the amount of the relative change in clearance in the event of a change in dialysate rate is always greater in the case of operation in co-current flow than in countercurrent flow.

5 Claims, 2 Drawing Sheets

(56) References Cited

OTHER PUBLICATIONS

Di Filippo et al "Relationship between urea clearance and ionic dialysance determined using a single-step conductivity profile," Kidney International, vol. 68 (2005), pp. 2389-2395.*
International Search Report and Written Opinion issued in corresponding International Patent Application No. PCT/EP2015/066577 (with English translation of International Search Report) dated Oct. 21, 2015 (10 pages).
International Preliminary Report on Patentability for corresponding International Patent Application No. PCT/EP2015/066577, dated Feb. 7, 2017, with corresponding Form PCT/IB/338 and Written Opinion of the International Searching Authority (Form PCT/ISA/237) (8 pages total).

* cited by examiner

DEVICE FOR IDENTIFYING THE DIRECTION OF LIQUID FLOW THROUGH A DIALYSER

This application is a National Stage Application of PCT/EP2015/066577, filed Jul. 20, 2015, which claims priority to German Patent Application No. 10 2014 011 250.0, filed Aug. 1, 2014, which are incorporated in their entireties by reference herein.

The invention relates to a device and a method for detecting the direction of fluid flow through a dialyser which comprises a blood chamber, through which blood flows, and a dialysate chamber, through which dialysate flows, which are separated from one another by a semi-permeable membrane. In addition, the invention relates to an extracorporeal blood treatment device comprising an extracorporeal blood circuit, which includes the blood chamber of a dialyser divided into the blood chamber and a dialysate chamber by a semi-permeable membrane, and comprising a fluid system, which includes the dialysate chamber of the dialyser, the extracorporeal blood treatment device comprising a device for detecting the direction of fluid flow through the dialyser.

Various kinds of blood treatment devices are known. The known blood treatment devices include, for example, the devices for haemodialysis, haemofiltration and haemodiafiltration. During blood treatment, the patient's blood flows in an extracorporeal blood circuit through a blood treatment unit. In the case of devices for haemodialysis, haemofiltration and haemodiafiltration, the blood treatment unit is a dialyser or filter, which is divided into a blood chamber and a dialysate chamber by a semi-permeable membrane. During blood treatment, the blood flows through the blood chamber while the dialysate flows through the dialysate chamber. An effective blood treatment is conditional upon the blood and the dialysate flowing along the membrane of the dialyser or filter in opposite directions. The blood treatment is less effective with the same flow direction. Therefore, in practice, the dialyser or filter is not operated in co-current flow, but rather in countercurrent flow. However, in individual cases, reduced dialysis efficiency can also be desirable, for example in order to prevent disequilibrium syndrome. Operation can then take place in the co-current flow if the dialysis efficiency is not reduced by a change in the blood flow or dialysate flow. Also in the case of problems with the dialyser (clotting) a co-current connection can be advantageous. Furthermore, in the case of treatments using a combination of diffusive and convective exchange of substances (haemodiafiltration) there is the possibility of limiting the diffusive portion of the exchange of substances by operating in co-current flow.

Various physical and/or chemical values are known, using which the performance of a dialyser and/or the efficacy of a dialysis treatment can be specified. A known value for specifying the efficacy of a dialysis treatment is clearance K. The clearance K of a substance is the partial flow of the total flow through the dialyser which is fully cleared of the substance concerned. What is known as the KT/V is of decisive importance to the efficacy of a dialysis treatment and is defined as the quotient of the product of clearance K for urea and effective treatment time T of the dialysis treatment and the distribution volume V of the patient for urea.

Methods and devices for measuring the clearance during an extracorporeal blood treatment are known from DE 39 38 662 A1 (U.S. Pat. No. 5,100,554) and DE 197 47 360 A1 (U.S. Pat. No. 6,156,002). Determination of the clearance is based on the measurement of the electrolyte transfer in two different dialysate ion concentrations. It is known from these publications that the clearance depends on the dialysate flow. The clearance also depends on the blood flow, correctly only the effective serum flow (plasma water and intracellular water) being decisive.

The known dialysis devices allow the manual adjustment of different dialysate rates, for example 300, 500 and 800 ml/min. To achieve a high clearance, in principle higher dialysate flows are required with higher blood flows.

The dialyser or filter of a blood treatment device is an exchangeable unit which is connected to the fluid system of the dialysis device. The fluid system of the known blood treatment devices comprises a line system comprising a first and a second line portion for connection to the dialyser. To connect the dialyser to the fluid system, the first line portion is connected to the inlet of the dialysate chamber and the second line portion is connected to the outlet of the dialysate chamber of the dialyser.

The manufacturers of dialysers and blood treatment devices provide colour coding of the line portions to be connected to the inlet and outlet on both the blood side and the dialysate side in order to make countercurrent or co-current connection easier for the user. This colour coding, however, is not standard among all manufacturers. Therefore, there is a risk of the connections being confused. This is described in the following as an incorrect connection. The same applies to an automatic reversal of the flow direction, for example by switching a device provided in the extracorporeal blood circuit over to flow reversal or by reversing the conveying direction of the blood pump, since an incorrect connection can also occur here.

If the dialyser is not operated in countercurrent flow, but rather in co-current flow, the efficacy of the blood treatment may be insufficient for the patient. This can then be problematic in particular if an incorrect connection of the dialyser remains unnoticed. There is then risk of the patient not being treated with sufficient efficacy over a long time.

A mix-up of the connections is not readily discernible to the user. An expected reduction in efficiency during operation in co-current flow instead of countercurrent flow cannot be taken as an indicator of co-current flow operation since a reduction in dialysis efficiency can also be brought about by other factors, for example clotting of the dialyser or recirculation in vascular access and there is a lack of reference values that can be used in practice for the expected value of the dialysis efficiency.

DE 10 2010 032 980 A1 describes a device for detecting the flow direction of fluid through a dialyser on the basis of the change of a physical and/or chemical property, for example the substance concentration, of a fluid flowing into the blood chamber of the dialyser and the measurement of the change in the physical and/or chemical property of the fluid flowing out of the blood chamber of the dialyser. The change in the physical and/or chemical property of the fluid downstream of the blood chamber of the dialyser, which can be attributed to the change in the physical and/or chemical property upstream of the blood chamber of the dialyser, is measured before and after the reversal of the flow direction of the fluid through the blood chamber.

A device for detecting an operating state of an extracorporeal blood treatment device is known from WO 2012/159734 A1 and has a measuring unit for measuring the dialysis efficiency (clearance). The measurement of the clearance is based on the change of the properties of the fresh dialysate and the reaction that has taken place in the used dialysate at dialysis conditions specified by the user, for example a specified blood flow and dialysate flow.

WO 2012/159734 A1 also discloses calculating the clearance from the mass transfer coefficient $K_0A$ as a parameter for the efficiency of the dialyser, the dialysate flow $Q_d$ and the blood flow $Q_b$. This correlation describing the dependency of the clearance on the dialysate rate is known from WO 2012/159734 A1 for operation in countercurrent flow and co-current flow. The mass transfer coefficient is, however, not known in practice. A transmission of manufacturer specifications does not normally occur at the dialysis device. Even if the mass transfer coefficient $K_0A$ of the dialyser were intended to be known, the effective mass transfer coefficient $K_0A$, into which the blood and patient parameters are entered, is, however, relevant to the treatment.

In WO 2012/159734 A1, operation of the dialyser in co-current flow instead of countercurrent flow is also described as an incorrect operating state. At a blood flow of 300 ml/min and a dialysate flow of 500 ml/min, the clearance should reduce, for example, by 32% when using a known dialyser if the dialyser is operated in co-current flow rather than in countercurrent flow. If the deviation between the measured clearance and the clearance expected for countercurrent flow is in the range expected for co-current flow, a mix-up of the couplings of the dialyser can be presumed to be the cause of the fault. However, operation in co-current flow cannot be concluded merely in the event of a reduction in clearance, since a reduction in clearance can also be attributed to a recirculation in the vascular access or other causes.

The object of the invention is to provide a device and a method for detecting the direction of fluid flow through a dialyser in order to be able to check whether the dialyser is being operated in co-current flow or countercurrent flow.

In addition, an object of the invention is to produce an extracorporeal blood treatment device by means of which safety of the dialysis is increased.

These objects are achieved according to the invention by the features of the independent claims. Advantageous embodiments of the invention are the subject of the dependent claims.

A first aspect of the invention is to measure the clearance or a value characteristic of the clearance in order to detect the direction of fluid flow through the dialyser and to compare the measured clearance or the measured value characteristic of the clearance respectively with a specified limit value, the direction of blood flow through the blood chamber and dialysate flow through the dialysate chamber in countercurrent flow being concluded when the clearance or the value that is characteristic of the clearance is greater than the specified limit value. This aspect is based on the finding that in the event of blood treatment in practice with co-current flow operation of the dialyser, clearance values above a certain limit value are no longer achievable. Therefore, operation in countercurrent flow can immediately be concluded for clearance values above a specified limit value. Consequently, it can be seen immediately whether the dialyser has also actually been set to operate in countercurrent flow, which is predominantly customary in practice. As a result, the safety of the blood treatment can be increased.

The specified limit value can be determined for a certain range in which changes in the dialysate flow and/or blood flow are to be expected in practice. In the process, the mass transfer coefficient of the dialysers used in practice can be taken into account.

To measure the clearance or a value characteristic of the clearance, the device according to the invention has a measuring unit, and to compare the measured clearance with the specified limit value, it has an evaluation and arithmetic unit. The measuring unit and the evaluation and arithmetic unit can form independent units or else be a component of the measuring device and/or the central control unit and/or arithmetic and evaluation unit (microprocessor) of the blood treatment device.

A second aspect of the invention, in order to detect the flow direction, is to measure the clearance or a value characteristic of the clearance and to change the flow rate of the dialysate. For this purpose, the device according to the invention has a measuring unit to measure the clearance or a value characteristic of the clearance before and after the change in dialysate rate and a control unit to change the flow rate of the dialysate through the dialysate chamber of the dialyser by a specified amount.

The device according to the invention and the method according to the invention in accordance with the second aspect of the invention are based on the comparison of the change in the measured clearance or in a value characteristic of the clearance with a calculated expected value of the change in clearance or in a value characteristic of the clearance for an operation of the dialyser both in countercurrent flow and in co-current flow. An actual operation of the dialyser in countercurrent flow is then concluded if the measured value for the change in clearance or in the value characteristic of the clearance is closer to the expected value for the change in clearance or in the value characteristic of the clearance for countercurrent flow operation than for co-current flow operation, while an actual operation of the dialyser in countercurrent flow is concluded if the measured value for the change in clearance or in the value characteristic of the clearance is closer to the expected value for the clearance or for the value characteristic of the clearance for co-current flow operation than for countercurrent flow operation. The invention according to the second aspect is based on the finding that the amount of the relative change in clearance in the event of a change in dialysate rate during operation in co-current flow is always greater than in countercurrent flow.

It is of no significance to the invention how the current value of the clearance is measured. For this purpose, all methods known from prior art can be used. In this connection, a measurement of the clearance is also understood to mean the determination of the clearance, if the clearance is calculated from measured values.

The arithmetic and evaluation unit of the device according to the invention is configured such that on the basis of the change in clearance or in the value characteristic of the clearance, which is attributable to the change in dialysate rate by a specified amount, a conclusion is made about the direction of blood flow through the blood chamber and dialysate flow through the dialysate chamber in countercurrent flow or co-current flow.

In a preferred embodiment of the invention, the amount of the change to be expected in clearance, which is attributable to the change in dialysate rate, or in the value characteristic of the clearance is calculated on the basis of a correlation describing the dependency of the clearance or of the value characteristic of the clearance on the dialysate rate for a countercurrent and co-current flow of the dialysate, and the amount of the actual change in clearance or in the value characteristic of the clearance is calculated from the clearance or the value characteristic of the clearance measured before and after the change in dialysate rate. On the basis of a comparison of the amount of the actual change in the clearance or in the value characteristic of the clearance with the expected value of the change in clearance or in the value characteristic of the clearance for countercurrent flow and co-current flow, a conclusion is then made about a countercurrent flow or co-current flow. Various methods of evaluation can be used for the comparison of the actual change and the calculated change in clearance.

In a preferred embodiment, the amount of the difference between the amount of the actual change in the clearance or in the value characteristic of the clearance and the expected value of the change in clearance or in the value characteristic of the clearance for countercurrent flow and the amount of the difference between the amount of the actual change in clearance or in the value characteristic of the clearance and the expected value of the change in clearance or in the value characteristic of the clearance for co-current flow is calculated. A co-current flow is then concluded if the amount of the difference for the co-current flow is smaller than the amount of the difference for countercurrent flow, while a countercurrent flow is concluded if the amount of the difference for countercurrent flow is smaller than the amount of the difference for co-current flow. Consequently, it is checked whether the measured change in clearance is closer to the expected value for the co-current flow operation or countercurrent flow operation.

The measuring unit for measuring the clearance or the value characteristic of the clearance preferably has means to change a physical and/or chemical property of the dialysate flowing into the dialysate chamber and means for measuring the physical and/or chemical property of the dialysate flowing out of the dialysate chamber. The physical and/or chemical property is preferably the concentration of a substance in the dialysate, the means for measuring the physical and/or chemical property being means for measuring the substance concentration. To detect the flow direction of the dialyser it is in principle insignificant which physical and/or chemical property is changed. Preferably, the Na concentration is changed.

The substance quantity can easily be changed in the dialysate preparation of the extracorporeal blood treatment device. The concentration of a substance can be measured using the known sensors which are generally present in the known blood treatment devices in any case. Therefore, the method according to the invention and the device according to the invention can easily be implemented in the known blood treatment devices.

Instead of the change in substance concentration, the clearance can also be measured using a measuring unit, which measures the value characteristic of the clearance, for example the absorption of electromagnetic radiation in the blood, which can be in the UV range, visible range or IR range.

In a further preferred embodiment, after determining the flow direction, the arithmetic and evaluation unit generates a signal (data) indicating the operating state in countercurrent flow or the operating state in co-current flow. This signal (data) can be transmitted to an external unit. In a particularly preferred embodiment, the signal is transmitted to a display unit displaying the operating state. The signal can, however, also be a control signal which the central control unit of the blood treatment device receives in order to perform an intervention in the machine control system. The intervention in the machine control system can be that the blood treatment is prevented from being carried out. It is thereby ensured that the blood treatment is only possible in the case of proper connection of the dialyser. It is, however, also possible for the intervention in the machine control system to be to reverse the flow direction so that the dialyser can then be operated correctly. The signal can also be an alarm signal in order to give an alarm in the event of an incorrect connection of the dialyser.

The first and second aspect of the invention can be used as independent criteria for checking the flow direction, or in combination. Preferably, both aspects are combined with one another for checking the flow direction. Firstly, it can be checked according to the first aspect whether the clearance is above the specified limit value. If this is the case, a check according to the second aspect can be omitted. The check according to the second aspect can, however, act as the verification of the check according to the first aspect or vice versa.

Figure 2:
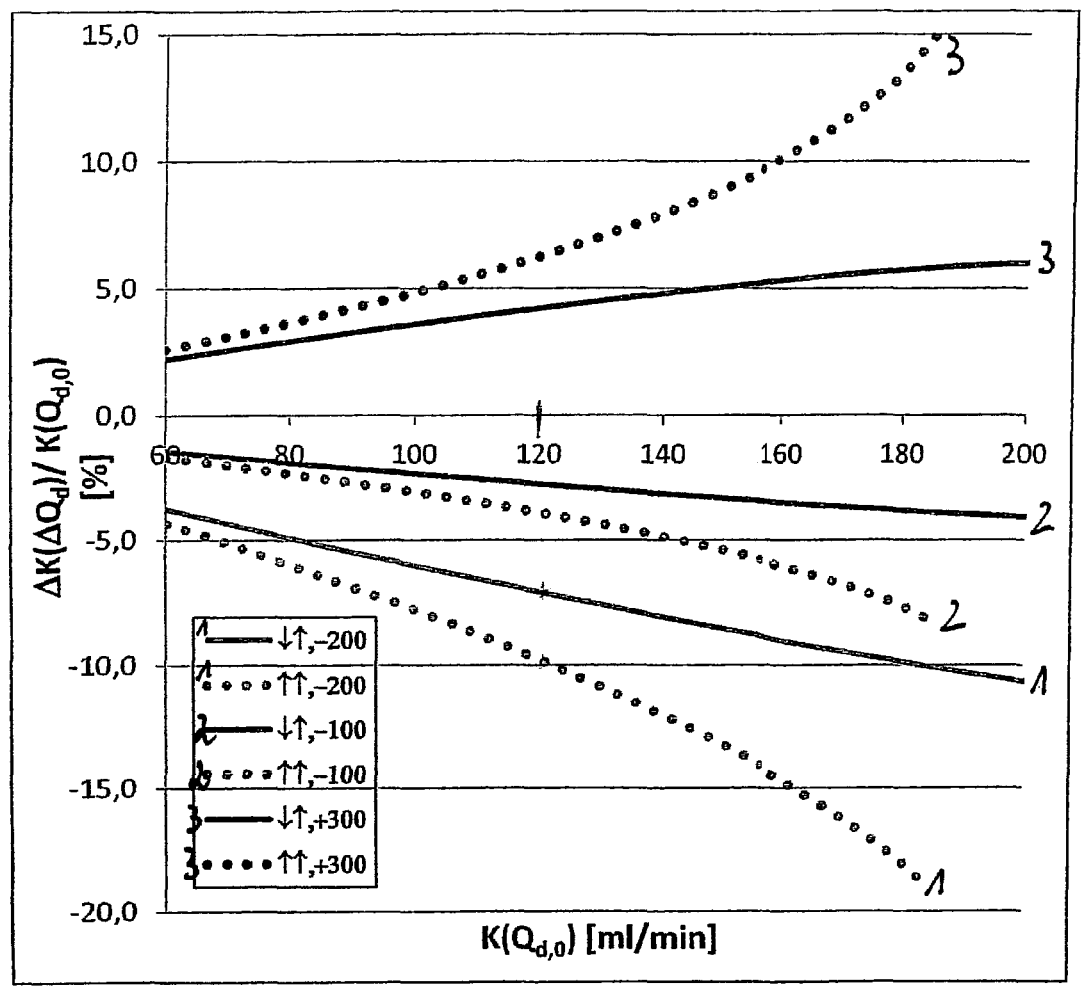

An embodiment of the invention is described in the following with reference to the drawings, in which:

FIG. 1 is a greatly simplified schematic view of the essential components of an extracorporeal blood treatment device and FIG. 2 shows the relative change in clearance in the event of a change of dialysate rate for the operation of the dialyser in co-current flow and in countercurrent flow.

FIG. 1 is a greatly simplified schematic view of only those components that are essential to the invention of an extracorporeal blood treatment device. In the present embodiment, the device for detecting the direction of fluid flow through the dialyser of the extracorporeal blood treatment device is a component of the blood treatment device. The device for detecting the flow direction through the dialyser can, however, also constitute a separate unit.

The extracorporeal blood treatment device, which is a haemodialysis device in the present embodiment, has a dialyser 1, which is separated by a semi-permeable membrane 2 into a blood chamber 4 and a dialysate chamber 3. The blood chamber 4 has a first port 4A and a second port 4B, while the dialysate chamber 3 has a first port 3A and a second port 3B.

The fluid system has a device 5, which is only shown schematically, by means of which fresh dialysate is produced from water and concentrates. The device 5 for preparing fresh dialysate allows a quick change, in particular an increase in the concentrate composition, in order to produce a concentrate bolus.

The device 5 for preparing fresh dialysate is connected via a first dialysate line 6 to the first port 3A of the dialysate chamber 3. A second dialysate line 7, in which a dialysate pump 8 is connected, leads from the second port 3B of the dialysate chamber 3 to an outlet 9. This part of the blood treatment device constitutes the dialysate system I.

An arterial blood line 10, in which a blood pump 11 is connected, leads from the patient to the first port 4A of the blood chamber 4, while a venous blood line 12, which leads back to the patient, leaves from the second port 4B of the blood chamber 4. This part of the blood treatment device constitutes the extracorporeal blood circuit II.

During the extracorporeal blood treatment, dialysate flows through the dialysate chamber 3 and blood flows through the blood chamber 4. In the process, dialysate and blood flow along the membrane 2 of the dialyser 1. In order to increase the efficiency of the treatment, the dialyser 1 is generally operated in countercurrent flow. In the process, dialysate and blood flow along the membrane in opposite directions. The dialyser can, however, also in principle be operated in co-current flow.

The blood treatment device has a central control unit 13, which is connected to the dialysate pump 8 and the blood pump 11 via control lines 8', 11'.

The first and second dialysate lines 6, 7 are hose lines, to which the dialyser 1 is connected. Connectors, which are not shown, in particular Hansen couplings, which are generally colour coded, serve to connect the hose lines 6, 7 to the ports 3A, 3B of the dialyser 1.

The device for detecting the flow direction through the dialyser 1, which in the present embodiment is a component of the blood treatment device, has an arithmetic and evaluation unit 14, which is connected to the central control unit 13 of the blood treatment device via a data line 15. The arithmetic and evaluation unit 14 can, however, also be a component of the central control unit 13. In addition, the device for detecting the flow direction has a control unit for changing the dialysate rate by a specified amount, which in this embodiment is a component of the central control unit 13 of the blood treatment device, but can also be a separate unit.

The dialysate system I can comprise a device 16 for reversing the flow direction, which has an arrangement of valves 16A, 16B, 16C, 16D. The valves are preferably electromagnetically or pneumatically actuated valves which are controlled via control lines 16A', 16B', 16C', 16D' by the central control unit 13 of the blood treatment device.

The valve 16A is arranged in the first dialysate line 6 and the second valve 16B is arranged in the second dialysate line 7. Upstream of the first valve 16A, a first line branch 6A branches off from the first dialysate line 6 and leads to the second dialysate line 7 upstream of the second valve 16B. The third valve 16C is connected in the first line branch 6A. Downstream of the first valve 16A, a second line branch 6B branches off from the first dialysate line 6 and leads to the second dialysate line 7 downstream of the second valve 16B. The fourth valve 16D is connected in the second line branch 6B. In the process, the terms "upstream" and "downstream" of the valves relate to the flow direction when the fluid flow is not reversed.

In normal operation, the dialyser 1 is operated in countercurrent flow. For this purpose, the central control unit 13 opens the first and second valve 16A, 16B and closes the third and fourth valve 16C, 16D. Consequently, the first port 3A is the inlet and the second port 3B is the outlet of the dialysate chamber 3. To reverse the flow direction, the control unit 13 closes the first and second valve 16A, 16B and opens the third and fourth valve 16C, 16D. Then the first port 3A is the outlet and the second port 3B is the inlet of the dialysate chamber 3.

The device for detecting the flow direction of the dialyser has a measuring unit for measuring the clearance, which measuring unit has means to measure a physical and/or chemical property of the dialysate. In the present embodiment, the physical and/or chemical property of the dialysate is the concentration of a substance in the dialysate, for example the sodium concentration. To measure the physical and/or chemical property, means 17 are provided, which comprise a first sensor 17A and a second sensor 17B. In order to determine the Na concentration, the first sensor 17A measures the conductivity of the dialysate in the first dialysate line 6 upstream of the dialyser 1, while the second sensor 17B measures the conductivity of the dialysate in the second dialysate line 7 downstream of the dialyser 1. The sensors 17A, 17B are connected to the arithmetic and evaluation unit 14 via data lines 17A', 17B'.

In addition, a display unit 18A and an alarm unit 18B are provided and are connected via data lines 19A and 19B to the arithmetic and evaluation unit 14. The display unit 18A displays the operation of the dialyser in co-current flow or countercurrent flow. The alarm unit 18 gives an alarm if an incorrect operation of the dialyser 1 is ascertained.

Firstly, the theoretical principles of the detection of the flow direction through the dialyser are explained.

In countercurrent flow operation, the effective dialyser parameter (mass transfer coefficient) $K_0A$ can be calculated from a first measurement of the diffusive clearance $K_{diff,1}$ when the dialysate flow $Q_{d,0}$ and blood (water) flow $Q_{bw}$ are known (Sargent/Gotch "Principles and Biophysics of Dialysis" in "Replacement of Renal Function by Dialysis"):

$$k_0 A_{\downarrow\uparrow} = \frac{Q_{bw} Q_{d,0}}{Q_{d,0} - Q_b} \ln\left(\frac{\frac{K_{diff,1}}{Q_{d,0}} - 1}{\frac{K_{diff,1}}{Q_{bw}} - 1}\right) \quad \text{Equation (1)}$$

In co-current flow operation, the corresponding correlation is:

$$(k_0 A)_{\uparrow\uparrow} = -\frac{Q_{bw} Q_{d,0}}{Q_{d,0} + Q_{bw}} \ln\left(1 - K_{diff,1}\left(\frac{1}{Q_{bw}} + \frac{1}{Q_{d,0}}\right)\right) \quad \text{Equation (2)}$$

Assuming that the mass transfer coefficient $K_0A$ remains constant in the event of a change of dialysate flow $Q_d$, in the event of a change in the dialysate flow by $\Delta Q_d$ the expected value of the diffusive clearance $\tilde{K}_{diff,2}$ can now be calculated both for countercurrent flow operation and for co-current flow operation:

$$(\tilde{K}_{diff,2})_{\downarrow\uparrow} = Q_{bw} \frac{e^{\gamma_{\downarrow\uparrow}} - 1}{e^{\gamma_{\downarrow\uparrow}} - \frac{Q_{bw}}{Q_{d,0} + \Delta Q_d}}, \quad \text{Equation (3)}$$

$$\gamma_{\downarrow\uparrow} = (k_0 A)_{\downarrow\uparrow} \frac{(Q_{d,0} + \Delta Q_d) - Q_{bw}}{Q_{bw}(Q_{d,0} + \Delta Q_d)}$$

$$(\tilde{K}_{diff,2})_{\uparrow\uparrow} = Q_{bw} \frac{1 - e^{\gamma_{\uparrow\uparrow}}}{1 + \frac{Q_{bw}}{Q_{d,0} + \Delta Q_d}}, \quad \text{Equation (4)}$$

$$\gamma_{\uparrow\uparrow} = (k_0 A)_{\uparrow\uparrow} \frac{(Q_{d,0} + \Delta Q_d) + Q_{bw}}{Q_{bw}(Q_{d,0} + \Delta Q_d)}$$

The device according to the invention and the method according to the invention can be used not only for detecting the flow direction for haemodialysis (HD), but also for haemodiafiltration (HDF). In the case of an HDF treatment having a predilution or post dilution, the diffusive proportion of the clearance is extracted from the total clearance $K_m$ determined from the measurements. This is possible using the following equation and so the equations (1) to (4) can also be applied to HDF procedures.

$$K_{diff} = \frac{Q_{bw} + \kappa Q_s}{Q_b - Q_f - (1 - \kappa)Q_s}\left(\frac{Q_{bw} + \kappa Q_s}{Q_b} K_m - Q_f - Q_s\right),$$

κ=1 with HDF predilution
κ=0 with HD and HDF post dilution $Q_{bw}$ denotes the blood water flow, $Q_b$ the blood flow, $Q_d$ the dialysate flow, $Q_f$ the filtrate flow and $Q_S$ the substitute flow.

The general case of haemodiafiltration (HDF) is described in detail in Gross, Maierhofer et al. "Online clearance measurement in high-efficiency hemodiafiltration" (Kidney International (2007) 72, 1550-1553).

Following a second determination of the diffusive clearance $K_{diff,2}$ at a dialysate flow of $Q_{d,0}+\Delta Q_d$ the real change in the diffusive clearance $\Delta K_{diff}=K_{diff,2}-K_{diff,1}$ for co-current flow operation and countercurrent flow operation can now be compared with the expected change $\Delta(\tilde{K}_{diff})$ for co-current flow operation and countercurrent flow operation.

$$\Delta(\tilde{K}_{diff})_{\downarrow\uparrow}=(\tilde{K}_{diff,2})_{\downarrow\uparrow}-(\tilde{K}_{diff,1})_{\downarrow\uparrow} \text{ and}$$

$$\Delta(\tilde{K}_{diff})_{\downarrow\uparrow}=(\tilde{K}_{diff,2})_{\downarrow\uparrow}-(\tilde{K}_{diff,1})_{\uparrow\uparrow}$$

FIG. 2 shows the relative change in clearance in the event of a change in dialysate rate $Q_d$ by −200 ml/min, −100 ml/min (reduction) and +300 ml/min (increase) from a specified, original dialysate rate $Q_d$ of 500 ml/min and a specified blood flow rate $Q_b$ of 300 ml/min with operation of the dialyser 1 in countercurrent flow $\downarrow\uparrow$ and with operation in co-current flow $\uparrow\uparrow$ for a haemodialysis treatment (HD). The clearance K at the original dialysate rate of 500 ml/min is entered on the x axis. The determined values of the clearance K are between 60 and 200 ml/min. It can be seen that in the event of a blood treatment in practice with operation of the dialyser in the co-current flow, clearance values above a limit value of 185 ml/min can no longer be achieved. Furthermore, it can be seen that the amount of the relative change in clearance in the event of a change of the dialysate rate with operation in co-current flow is always greater than countercurrent flow.

For dialysers typically used in haemodialysis having a mass transfer coefficient $K_0A$ of 300-1200 ml/min, a clearance K of at least 150 ml/min is also to be expected in co-current flow before the change in dialysate rate $Q_b$. Therefore, in the present example, in the event of changes in the dialysate rate $Q_b$ of −200 and +300 ml/min (to 300 and 800 ml/min) the difference in clearance change between co-current and countercurrent flow lies outside of the error tolerance of a clearance determination on the basis of conductivity.

The central control unit 13 and the arithmetic and evaluation unit 14 are configured such that the individual steps of the method according to the invention for detecting the flow direction are carried out.

In the embodiment, it is assumed that the dialyser 1 is intended to be operated in countercurrent flow. Countercurrent flow operation is therefore the normal operation. This is to be checked in the present embodiment.

In the event of a certain blood flow rate $Q_b$ and a certain dialysate rate $Q_{d,0}$, which are specified for the blood treatment, the measuring unit measures the diffusive clearance $K_{diff,1}$. For this purpose, by means of a short-term change in the concentration composition in the device 5 in order to prepare fresh dialysate in the dialysis circuit I upstream of the dialyser, a concentrate bolus is produced which is measured by the sensors 17A and 17B of the measuring unit upstream and downstream of the dialyser 1. The sensor 17A upstream of the dialyser 1 can also be omitted if the value of the bolus is known. The measuring unit then calculates the clearance $K_{diff,1}$ from the ascertained measured values. The calculation of the clearance from the measured values forms part of the prior art (DE 39 38 662 A1, DE 197 47 360 A1).

Firstly, the arithmetic and evaluation unit 14 compares the measured clearance $K_{diff,1}$ with a specified limit value, which is above 160 ml/min, preferably above 175 ml/min, most preferably above 185 ml/min. If the clearance $K_{diff,1}$ is above the limit value, the arithmetic and evaluation unit 14 concludes operation in countercurrent flow, since such a high value for the clearance cannot be achieved in co-current flow operation, which can, however, be checked again subsequently. Otherwise, co-current flow operation is concluded, which likewise can be checked again.

The dialysate rate $Q_d$ is now changed by a specified amount, i.e. the dialysate rate $Q_d$ is increased or reduced, the blood flow rate $Q_b$ being maintained. After the change in dialysate rate $Q_d$, the clearance $K_{diff,2}$ is measured again by the measuring unit.

The measured values $K_{diff,1}$ and $K_{diff,2}$ saved in a memory (not shown) of the arithmetic and evaluation unit 14. From the measured values $K_{diff,1}$ and $K_{diff,2}$ the arithmetic and evaluation unit 14 calculates the amount of the change in clearance $\Delta(K_{diff})_{\downarrow\uparrow}$ resulting from the change in dialysate rate of $Q_d$ by the specified amount $\Delta Q_d$ to $Q_{d,0}+\Delta Q_d$ whilst maintaining the blood flow rate $Q_b$ for the assumed case of operation of the dialyser 1 in countercurrent flow:

$$\Delta(K_{diff})_{\uparrow\downarrow}=K_{diff,1}-K_{diff,2}$$

After determining the amount of the change in clearance $\Delta(\tilde{K}_{diff})_{\downarrow\uparrow}$ on the basis of the clearance measurements before and after the change in dialysate rate $Q_d$, the expected value of the clearance change is calculated both for the case of countercurrent flow $\Delta(\tilde{K}_{diff})_{\downarrow\uparrow}$ and for the case of co-current flow $\Delta(\tilde{K}_{diff})_{\uparrow\uparrow}$.

For this purpose, firstly, the mass transfer coefficient $K_0A$ of the dialyser 1 is calculated according to equation (1) for countercurrent flow and equation (2) for co-current flow from the previously measured clearance $K_{diff,1}$, the adjusted dialysate rate $Q_{d,0}$ and blood flow rate $Q_b$, and the blood water flow $Q_{bw}$.

Subsequently, the expected value of the clearance $(\tilde{K}_{diff,2})_{\downarrow\uparrow}$ for countercurrent flow after the change in dialysate flow is calculated from the dialysate rate increased by the specified amount $\Delta Q_d$ to $Q_{d,0}+\Delta Q_d$, the unchanged blood flow rate $Q_b$, the blood water flow $Q_{bw}$ and the previously determined mass transfer coefficient $K_0$ according to equation (3), and the expected value of the clearance $(\tilde{K}_{diff,2})_{\uparrow\uparrow}$ for co-current flow after the change in dialysate flow is calculated from the dialysate rate increased by the specified amount $\Delta Q_d$ to $Q_{d,0}+\Delta Q_d$, the unchanged blood flow rate $Q_b$, the unchanged blood water flow $Q_{bw}$ and the previously determined mass transfer coefficient $K_0A$ according to equation (4).

The arithmetic and evaluation unit 14 subsequently calculates the amount of the difference between the expected value of the clearance $(\tilde{K}_{diff,2})_{\downarrow\uparrow}$ for countercurrent flow after the change in dialysate rate and the clearance measured before the change in dialysate rate in order to determine the amount of the expected change in clearance for countercurrent flow, and calculates the amount of the difference between the expected value of the clearance $(\tilde{K}_{diff,2})_{\uparrow\uparrow}$ for co-current flow after the change in dialysate rate and the clearance measured before the change in dialysate rate in order to determine the amount of the expected change in clearance for co-current flow.

Subsequently, the arithmetic and evaluation unit 14 calculates the amount of the difference between the measured change in clearance and the expected value of the change in clearance for the case of countercurrent flow and calculates the amount of the difference between the measured change in clearance and the expected value of the change in clearance for the case of co-current flow.

The two difference values are then compared to one another. If the amount of the difference for countercurrent flow is smaller than the amount of the difference for co-current flow, the arithmetic and evaluation unit 14 concludes operation in countercurrent flow, which is the desired operation in the present embodiment. If, on the other hand, the amount of the difference for co-current flow is smaller than the amount of the difference for countercurrent flow, operation in co-current flow is concluded, which is not the desired operation in the present embodiment, i.e. it would be an erroneous state.

Moreover, the arithmetic and evaluation unit 14 generates a control signal indicating the operating state, which the display unit 18A receives and so the countercurrent flow or co-current flow operation is displayed.

If the dialyser 1 is incorrectly connected to the dialysate lines 6, 7, i.e. if the ports have been mixed up, the arithmetic and evaluation unit 14 generates a control signal, which the alarm unit 18B receives. The alarm unit 18B then gives an alarm. Moreover, the arithmetic and evaluation unit 14 generates a control signal, which the central control unit 13 receives. Then the control unit 13 carries out an intervention in the machine control system. This intervention can be that the performance of the blood treatment is interrupted. Alternatively, it is possible to reverse the flow direction by activating the corresponding valves 16A-16D, and so the dialyser is actually operated in countercurrent flow.

The invention claimed is:

1. A device for detecting the direction of fluid flow through a dialyzer, the device comprising
   a dialyzer that comprises a blood chamber, through which blood flows at blood flow rate $Q_{bw}$, and a dialysate chamber, through which dialysate flows at an initial dialysate flow rate $Q_{d,0}$, the blood chamber and the dialysate chamber being separated from one another by a semi-permeable membrane,
   a control unit for changing the flow rate of the dialysate through the dialysate chamber of the dialyzer from the initial dialysate flow rate to a second dialysate flow rate, $Q_{d,0}+\Delta Q_d$, selected by a user while maintaining the blood flow rate $Q_{bw}$ unchanged,
   a measuring unit that measures clearance at any dialysate flow rate, the measuring unit comprising: i) at least one conductivity sensor in a dialysate flow path upstream of the dialyzer, which measures a first conductivity of the dialysate, the dialysate having a first concentration of a substance, the first conductivity measured before the dialysate enters the dialyzer, and ii) at least one conductivity sensor in a dialysate flow path downstream of the dialyzer, which measures a second conductivity of the dialysate, the dialysate downstream of the dialyzer having a second concentration of the substance, the device being configured to measure the second conductivity after the dialysate leaves the dialyzer, the measuring unit being configured to calculate: i) a first clearance value, $K_{diff,1}$, based on a difference between the first conductivity and the second conductivity measured at the initial dialysate flow rate $Q_{d,0}$; and ii) a second clearance value $K_{diff,2}$, based on a difference between the first conductivity and the second conductivity measured at the second dialysate flow rate $Q_{d,0}+\Delta Q_d$, and
   an arithmetic and evaluation unit, comprising a microprocessor and a memory, the arithmetic and evaluation unit: i) calculating a change in clearance values, $\Delta K_{diff,1}$, by subtracting the first clearance value $K_{diff,1}$ from the second clearance value $K_{diff,2}$; ii) calculating a countercurrent mass transfer coefficient, $k_oA_{\uparrow\downarrow}$ based on $K_{diff,1}$, $Q_{d,0}$, and $Q_{bw}$; iii) calculating a co-current mass transfer coefficient, $k_oA_{\uparrow\uparrow}$ based on $K_{diff,1}$, $Q_{d,0}$, and $Q_{bw}$; iv) calculating a first expected change in a clearance value, $\Delta \acute{K}_{diff1}$, when the dialysate and blood flow are in countercurrent flow; v) calculating a second expected change in clearance value, $\Delta \acute{K}_{diff2}$, when the dialysate and blood flow are in co-current flow; and vi) comparing $\Delta K_{diff1}$ to each of $\Delta \acute{K}_{diff1}$ and $\Delta \acute{K}_{diff2}$, where if $\Delta K_{diff1}$ is Closer to $\Delta \acute{K}_{diff1}$ than $\Delta \acute{K}_{diff2}$, the arithmetic and evaluation unit determines that the dialysate flow and blood flow are in countercurrent flow, but if $\Delta K_{diff1}$ is closer to $\Delta \acute{K}_{diff2}$ than $\Delta \acute{K}_{diff1}$, the arithmetic and evaluation unit determines that the dialysate flow and blood flow are in co-current flow,
   wherein arithmetic and evaluation unit is configured to generate a control signal indicating co-current flow or countercurrent flow, and
   wherein the device further comprises a display unit, the display unit being configured to receive the control signal and, based on the control signal, display whether the operation of the dialyzer is in co-current flow or countercurrent flow.

2. The device according to claim 1, wherein the arithmetic and evaluation unit is configured to calculate the countercurrent mass transfer coefficient $k_0A_{\uparrow\downarrow}$ based on $K_{diff,1}$, $Q_{d,0}$, and $Q_{bw}$, by using a first equation, the first equation being $$k_0A_{\downarrow\uparrow} = \frac{Q_{bw}Q_{d,0}}{Q_{d,0}-Q_b}\ln\left(\frac{\frac{K_{diff,1}}{Q_{d,0}}-1}{\frac{K_{diff,1}}{Q_{bw}}-1}\right).$$

3. The device according to claim 1, wherein the arithmetic and evaluation unit is configured to calculate the co-current mass transfer coefficient $k_0A_{\uparrow\uparrow}$ based on $K_{diff,1}$, $Q_{d,0}$, and $Q_{bw}$, by using a second equation, the second equation being $$(k_0A)_{\uparrow\uparrow} = -\frac{Q_{bw}Q_{d,0}}{Q_{d,0}+Q_{bw}}\ln\left(1-K_{diff,1}\left(\frac{1}{Q_{bw}}+\frac{1}{Q_{d,0}}\right)\right).$$

4. The device according to claim 1, wherein the arithmetic and evaluation unit is configured to calculate the first expected change in the clearance value, $\Delta \acute{K}_{diff1}$, by using a third equation, the third equation being $$(\tilde{K}_{diff,2})_{\downarrow\uparrow} = Q_{bw}\frac{e^{\gamma_{\downarrow\uparrow}}-1}{e^{\gamma_{\downarrow\uparrow}}-\frac{Q_{bw}}{Q_{d,0}+\Delta Q_d}}, \gamma_{\downarrow\uparrow}=(k_0A)_{\downarrow\uparrow}\frac{(Q_{d,0}+\Delta Q_d)-Q_{bw}}{Q_{bw}(Q_{d,0}+\Delta Q_d)}.$$

5. The device according to claim 1, wherein the arithmetic and evaluation unit is configured to calculate the second expected change in the clearance value, $\Delta \acute{K}_{diff2}$, by using a fourth equation, the fourth equation being $$(\tilde{K}_{diff,2})_{\uparrow\uparrow} = Q_{bw}\frac{1-e^{-\gamma_{\uparrow\uparrow}}}{1+\frac{Q_{bw}}{Q_{d,0}+\Delta Q_d}}, \gamma_{\uparrow\uparrow}=(k_0A)_{\uparrow\uparrow}\frac{(Q_{d,0}+\Delta Q_d)+Q_{bw}}{Q_{bw}(Q_{d,0}+\Delta Q_d)}.$$

* * * * *